United States Patent [19]

Izumi

[11] Patent Number: 4,531,939
[45] Date of Patent: Jul. 30, 1985

[54] VACUUM SUCTION TYPE URINATING AID

[75] Inventor: Yoshitaka Izumi, Tokyo, Japan

[73] Assignee: Kimura Bed Mfg. Company Limited, Tokyo, Japan

[21] Appl. No.: 179,877

[22] Filed: Aug. 20, 1980

[30] Foreign Application Priority Data

Oct. 12, 1979 [JP] Japan .................. 54-140957[U]
Oct. 12, 1979 [JP] Japan .................. 54-140960[U]

[51] Int. Cl.³ .............................................. A61M 1/06
[52] U.S. Cl. ..................................... 604/73; 604/317; 4/305
[58] Field of Search .............. 128/295, 276, 277, 278, 128/138 A, 760; 4/301, 302, 305, 313, 144.1, 144.2, 144.3, 144.4, 431; 604/317, 327, 331, 346, 347, 349, 73

[56] References Cited

U.S. PATENT DOCUMENTS

| 3,114,916 | 12/1963 | Hadley | 4/144.3 |
| 4,033,338 | 7/1977 | Igwebike | 128/276 |
| 4,163,449 | 8/1979 | Regal | 128/138 A |
| 4,164,795 | 8/1979 | Johnson | 4/144.2 |
| 4,281,655 | 8/1981 | Terauchi | 128/278 |
| 4,345,342 | 8/1982 | Saito | 604/349 |
| 4,443,217 | 4/1984 | Izumi | 604/73 |
| 4,471,498 | 9/1984 | Robershaw | 4/302 |

FOREIGN PATENT DOCUMENTS

| 992462 | 10/1951 | France | 128/295 |
| 223258 | 10/1968 | U.S.S.R. | 128/295 |

Primary Examiner—C. Fred Rosenbaum
Assistant Examiner—J. L. Kruter
Attorney, Agent, or Firm—Wenderoth, Lind & Ponack

[57] ABSTRACT

A vacuum suction type urinating device includes a urine receiver provided with a urine suction opening to be applied to a urinating region, with an air suction hole and with a urine outlet. A urine transport tube is connected, at one end, with the urine outlet and is connected, at the other end, with a urine tank. A vacuum suction tube communicating to a vacuum suction device and is connected to the upper part of the urine tank. The vacuum suction device controlled by a control circuit provided with a start switch and a off delay timer.

3 Claims, 3 Drawing Figures

VACUUM SUCTION TYPE URINATING AID

BACKGROUND OF THE INVENTION

The present invention relates to a vacuum suction type urinating aid.

There are people who must be assisted in urinating in bed. These people include the old lying in bed, serious patients, patients suffering from incontinence of urine, who cannot control their urination as soon as they feel a desire to urinate, and patients who cannot go to the toilet alone.

To attain the objective of assistance, there is known an apparatus in which a receiver applied to the urinating region of the patient to receive his urine is connected with a tank to collect the urine through a tube. However, with the conventional apparatus, the urine received by the receiver is dropped into the tank through the tube simply by gravity, and therefore the tube and the tank must be placed below the receiver, to permit urine to be dropped. For example, if the patient changes his position, causing the tube to be placed even partially above the receiver, the urine in the tube flows back into the receiver, to soak the patient and bedclothes inconveniently. Such a conventional apparatus is disadvantageously restricted in the place of use and urinating pose.

SUMMARY OF THE INVENTION

The urinating aid of the present invention receives the urine of the patient in a urine receiver applied to his urinating region; and transports it to a urine tank through a urine transport tube forcedly together with air by vacuum suction, thereby overcoming the disadvantage of the conventional apparatus. In other words, even when the said urine transport tube and the urine tank cannot be placed below the urine receiver, the present invention allows urine to be transported into the urine tank, without causing it to flow back.

Particularly, the present invention has a feature that even if the start switch of the vacuum suction device is turned off after the end of urination, the vacuum suction device is automatically held in the state of operation for a while, to eliminate all the urine remaining in the urine transport tube, and therefore to prevent back flow of the urine with the vacuum suction device immediately stopped.

BRIEF DESCRIPTION OF THE DRAWINGS

The present invention is described below in detail with reference to the accompanying drawings which show preferred embodiments.

DETAILED DESCRIPTION OF THE INVENTION

Figure 1:
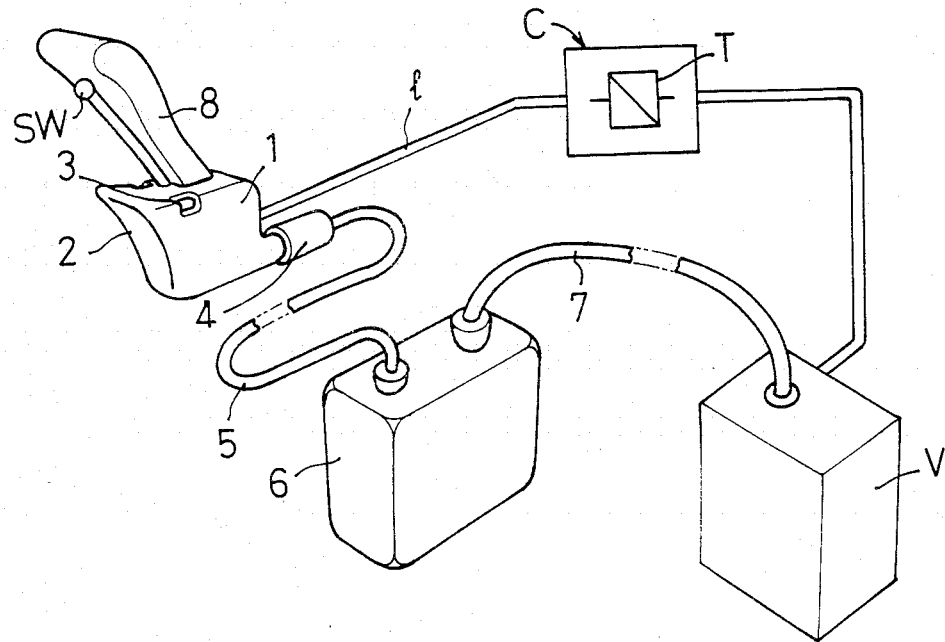
FIG. 1 is an illustrative perspective view to showing an embodiment of the general composition of the present invention.
Figure 2:
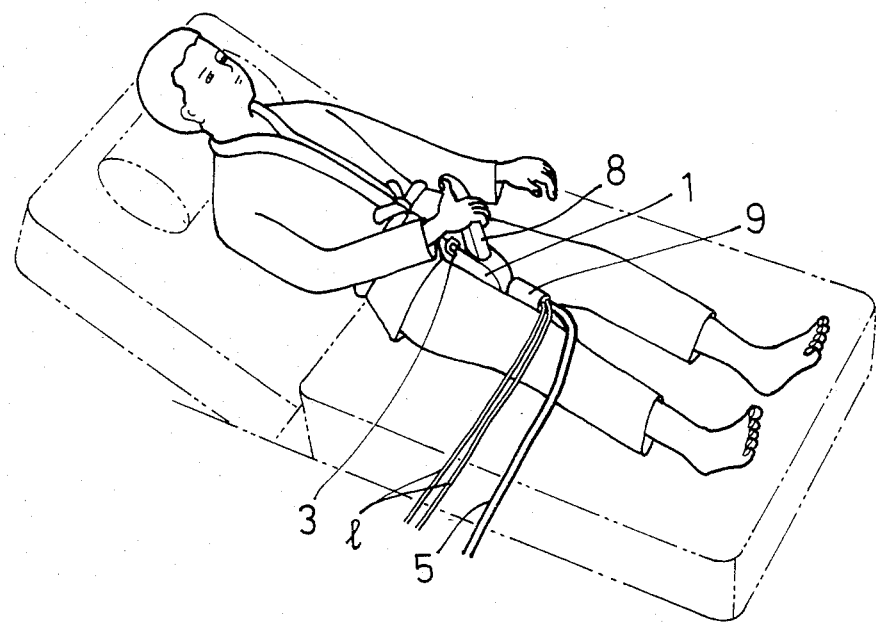
FIG. 2 is an illustrative perspective view showing the manner of use of the invention.
Figure 3:
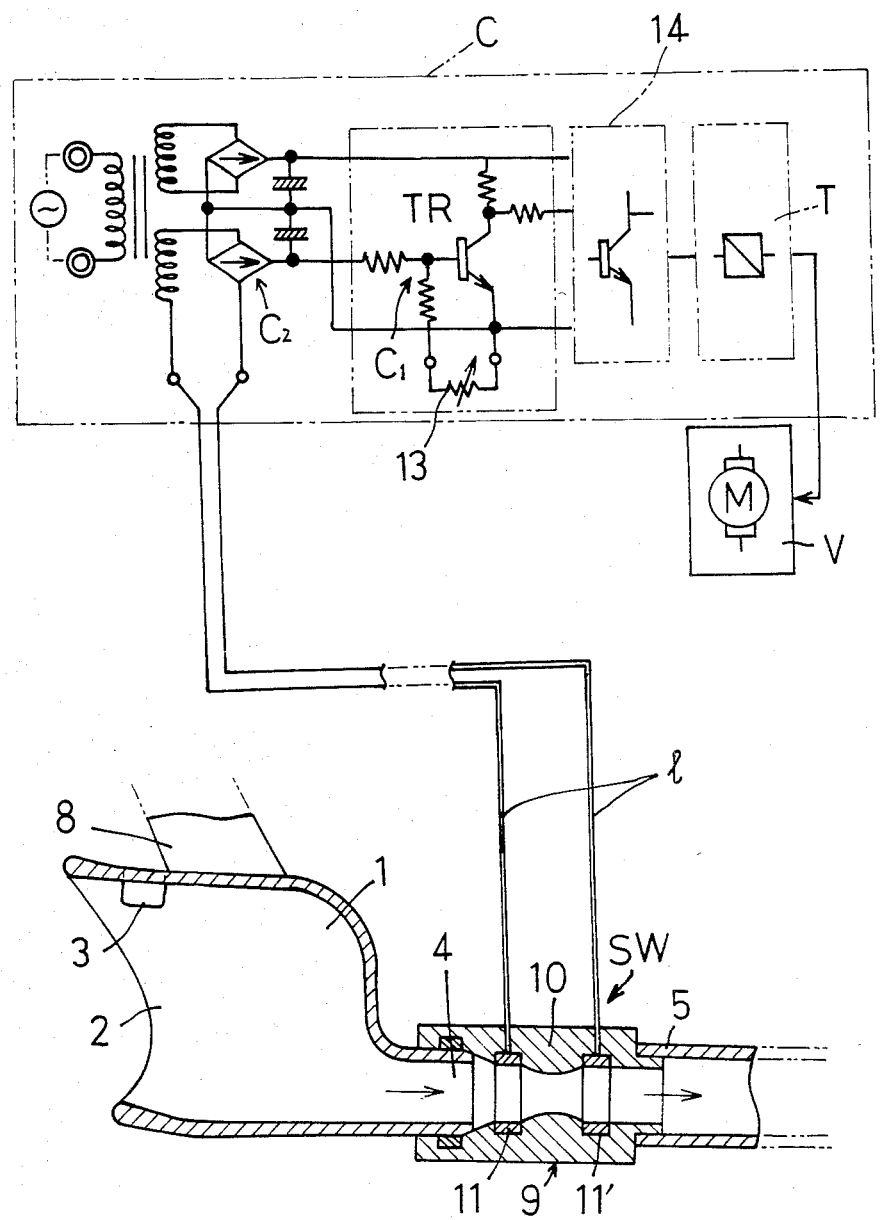
FIG. 3 is a sectional view and a systematic illustration showing an embodiment of a switching circuit.

In the drawing there is shown a urine receiver 1 provided with a urine suction opening 2 to be applied to a urinating region and with an air suction hole 3, and a urine transport tube 5 connected, at one end, with urine outlet 4 of urine receiver 1 and connected, at the other end, with a urine tank 6. Urine tank 6 is connected, at its upper part, with a vacuum suction tube 7 communicating to a vacuum suction device V. Vacuum suction device V is controlled by a control circuit C provided with a start switch SW and an off delay timer T. In the embodiment shown in FIG. 1, an ordinary manual switch set in a handle 8 of urine receiver 1 is used as the start switch, and in the embodiment shown in FIG. 3, an automatic switch to be described later is used. The connection between the start switch SW and the control circuit C and the wiring disposed between control circuit C and the vacuum suction device V can be made as desired, and for example, if the wiring is made along the urine transport tube 5, it will not be obstructive and will be excellent in appearance. The embodiment of FIG. 3 is described below.

Urine receiver 1 is provided with urine suction opening 2 to be applied to a urinating region and air suction hole 3, and urine transport tube 5 is connected, at one end, with urine outlet 4 of urine receiver 1 through a urine detecting cylinder 9 forming a urine passage described later, and is connected, at the other end, with urine tank 6. Urine tank 6 is connected, at its upper part, with vacuum suction tube 7 communicating to a vacuum suction device V. Urine detecting cylinder 9 has a pair of electrodes 11 and 11' placed at an interval inside an electrically insulating cylinder 10. Electrodes 11 and 11' can be shaped like rings or any other form. The pair of electrodes constitute a start switch. In the start switch SW shown by this embodiment, said electrodes 11 and 11' are connected to the AC side of a rectifier circuit $C_2$ connected to the base circuit $C_1$ of a transistor TR, and when the resistance value is decreased by urine wetting the area between electrodes 11 and 11', the alternating current flowing between electrodes 11 and 11' is rectified, to supply base current to transistor TR, thus turning on transistor TR. But the start switch of the electrodes 11 and 11' can be composed in any other way. In this embodiment, since the current flowing between the electrodes is alternating current, the electrodes 11 and 11' can be prevented from being electrolytically corroded. Vacuum suction device V is controlled by the control circuit C provided with the start switch SW containing electrodes 11 and 11' and with the off delay timer T. The off delay timer T can be composed as desired. Symbol 13 indicates a variable resistor for adjusting the urine detecting sensitivity, and 14 indicates an amplifier.

The operation of the present invention is described below with reference to the embodiment of FIG. 3.

When a patient feels a desire to urinate, he takes the handle 8, to apply the urine suction opening 2 to his urinating region, and urinates into the urine receiver 1. When urine flows through the urine outlet 4 into the urine detecting cylinder 9, to wet the area between the pair of electrodes 11 and 11', the resistance value between electrodes 11 and 11' is decreased, to cause detection current to flow, operating the control circuit C and starting the vacuum suction device V. The urine thus received by the urine receiver is forcedly sucked from the urine outlet 4 through the urine detecting cylinder 9 into the urine transport tube 5, together with the air sucked from air suction hole 3 and the clearance between urine suction opening 2 and the urinating region, and is discharged into the urine tank 6 through urine transport tube 5. In this case, since the vacuum suction tube 7 communicating to the vacuum suction device V is connected to the upper part of the urine tank 6, urine is not sucked into vacuum suction tube 7, but is collected in the urine tank 6, and is separated from air. Futhermore, since the urine receiver 1 is provided with the air suction hole 3 in addition to the urine suction opening 2, it prevents the urine suction opening 1 from adhering to the urinating region of the patient which would otherwise be caused by the vacuum pressure, to improve the feeling of using the aid, and even if the urine suction opening 1 is in close contact with the urinating region without any clearance, the volume of air to carry urine can be always obtained by the air sucked through air suction hole 3. The opening of the air suction hole 3 can be made freely adjustable. In the present invention, even when the urine transport tube 5 and the urine tank 6 are not placed below the urine receiver 1, urine does not flow back, since the urine received by the urine receiver 1 is sucked forcedly together with sucked air through the urine outlet 4 into the urine transport tube and is discharged into the urine tank 6.

As an effect of this embodiment, since the vacuum suction device V is automatically started by detecting the existence of urine by the urine detecting cylinder 9, the operation is simple, and the patient himself can use the aid easily, being free from the inconvenience of forgetting to turn on the switch or failing to turn on the switch in time as in the case of using a manual switch. Moreover, since the urine detecting cylinder 9 is provided near the urine outlet 4 of the urine receiver 1, it cannot happen that the urine discharged into the urine receiver 3 is spilled before the vacuum suction device V is started.

After the end of urination, the manual start switch SW is turned off, or the start switch automatically operated by urine is turned off, to initiate the stop procedure of the vacuum suction device V. Vacuum suction device V continues the suction of urine, by automatically maintaining the state of operation for a period of time set by the off delay timer T. If the stop procedure of the vacuum suction device V is directly controlled by start switch SW, the vacuum suction device stops as soon as the start switch SW is manually turned off, or automatically is turned off with no urine remaining between the electrodes 11 and 11' in the embodiment of FIG. 3 immediately after the end of urination, and urine may remain in the urine transport tube 5, which may flow back and inconveniently be spilled outside through the urine receiver 1. However, in the present invention, as mentioned above, the vacuum suction device V is automatically kept in the state of operation for a period of time set by the off delay timer T, and the urine remaining in the urine transport tube 5 when the start switch SW is turned off after the end of urination can be discharged into the urine tank 5 perfectly during the set period of time, thus not allowing any valve to back flow.

As described above in detail, the vacuum suction type urinating aid of the present invention has a feature that even when the urine transport tube and the urine tank cannot be placed below the urine receiver, urine can be collected perfectly in the urine tank without causing the urine to flow back, and therefore that a patient can urinate while lying in bed with no restriction on the place of use or urinating pose, since the urine received by the urine receiver applied to the urinating region of the patient, etc. is transported forcedly together with air in the urine transport tube by vacuum suction to the urine tank.

Particularly the present invention has further an important feature that even if the start switch of the vacuum suction device is turned off after the end of urination, the vacuum suction device is automatically held in the state of operation for a while, to eliminate all the urine remaining in the urine transport tube, and therefore that the back flow of urine with the vacuum suction device stopped is prevented perfectly.

What is claimed is:

1. A vacuum suction type urinating aid comprising:
   a urine receiver having a urine suction opening adapted to be applied to the urinating region of a subject to receive therefrom urine, an air suction opening, and a urine outlet;
   a urine tank;
   a urine transport tube connected between said urine outlet and said urine tank;
   vacuum suction device means connected to said urine tank for drawing air into said urine receiver through said air suction hole therein and for drawing said air and any urine in said urine receiver through said urine outlet and said urine transport tube into said urine tank;
   control circuit means connected to said vacuum suction device means for controlling stopping and starting thereof;
   start switch means for transmitting a start signal to said control circuit means for starting operation of said vacuum suction device means, and for transmitting a stop signal to said control circuit means; and
   said control circuit means including off delay timer means connected to said start switch means for, upon receipt therefrom of said stop signal, delaying stopping of said vacuum suction device means, thereby to maintain operation of said vacuum suction device means for a predetermined period of time, and thus for ensuring withdrawal of all urine from said urine receiver and said urine transport tube.

2. A vacuum suction type urinating aid as claimed in claim 1, wherein said urine receiver includes a handle, and said start switch means includes a manual switch set in said handle.

3. A vacuum suction type urinating aid as claimed in claim 1, wherein said start switch means comprises an automatic switch including a pair of electrodes spacedly positioned adjacent said urine outlet, said automatic switch being operable to initiate said start signal when an electric current flows through urine existing between said pair of electrodes and operable to initiate said stop signal upon urine no longer existing between said pair of electrodes.

* * * * *